Nov. 17, 1970 G. MERRILL Plant Pat. 3,002
PEACH TREE
Filed Feb. 4, 1969
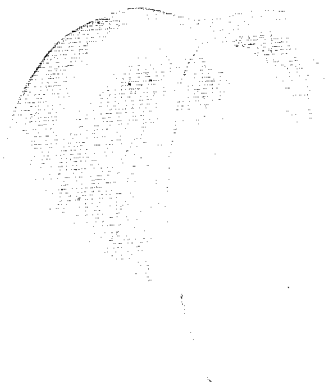
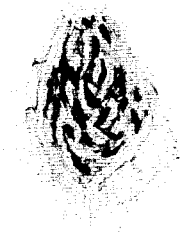
GRANT MERRILL
INVENTOR
Virgil L. Gerard
ATTORNEY

United States Patent Office

Plant Pat. 3,002
Patented Nov. 17, 1970

3,002
PEACH TREE

Grant Merrill, 416 N. Anderson Road,
Exeter, Calif. 93221

Filed Feb. 4, 1969, Ser. No. 796,620
Int. Cl. A01h *5/03*
U.S. Cl. Plt.—43 1 Claim

The present invention relates to a peach tree and more particularly to a new and distinct variety thereof broadly characterized by the late ripening of its freestone fruit which is fairly well colored and which has good characteristics as a frozen product.

The instant variety most nearly resembles Merrill Halloween No. 1 (U.S. Plant Pat. No. 1,473) but is distinguished therefrom and is an improvement thereon by reason of its having more red on the skin, showing better flesh color and texture when frozen, and having less tendency to drop as the fruit becomes ripe.

I originated the present variety on the form formerly owned by me at Red Bluff, Tehama County, Calif., by planting seeds of Kirkman Gem which produced a seedling, numbered 14–21 for reference purposes. Seeds of this seedling were then planted and these produced a seedling, numbered 77–110 for reference purposes, which is the instant variety.

The instant variety was asexually reproduced by grafting to a mature Elberta (unpatented) on my present farm at Exeter, Tulare County, Calif., and by grafting from the 77–110 seedling to a Red Globe (unpatented) on the K. Hiyama farm at Fowler, Fresno County, Calif. In each case, the present variety was exactly the same as the original fruit and tree (seedling 77–110).

The accompanying drawing is an oil painting of a characteristic mature fruit of the subject peach variety showing the shape and skin color, and by means of a fruit divided on its suture, showing flesh and stone color and characteristics.

Referring more specifically to the pomological characteristics of this new and distinct variety of peach tree, the following has been observed under the ecological conditions prevailing near Exeter, Tulare County, Calif., and is an outline description thereof. All major color plates are by reference to Maerz and Paul Dictionary of Color, 1st ed.

TREE

Shape: Large size, medium spreading.
Productiveness: Vigorous and productive, regular bearer, little fruit drop unless over-ripe.
Trunk: Medium stocky, shaggy, gray in color.
Branches: Gray and shaggy when old, brown and smoother when young.
Lenticels: Medium to small in size, numerous.

LEAVES (Selected from mid-portion of vigorous terminal shoots)
Shape: Lanceolate, tip accuminate.
Size: Medium size, length 4 to 8 inches, width 1⅛–2 inches, medium thick.
Color: Medium green on upper surface, lighter yellower green under surface, veins very light green.
Class (Meader & Blake: Proceedings of the American Society for Horticultural Science, vol. 37, p. 206): 1 for small leaves to 3 for largest leaves.
Margin: Granular, crenate.
Petiole: Medium size, medium length.
Glands: Reniform, alternate, medium large, at base of leaf and on petiole.
Character: Deciduous.

FLOWERS

Buds: Medium size, plump, free, pubescent.
Date of bloom: Generally late (in 1968, an early season, first blooms March 1, full bloom March 10).

Blooms: Large and showy, pink in color.
Pollen: Sparse.

FRUIT

Season of ripening: Late September to early October.
Size: Generally large, and globose but variable in size and shape; axial diameter, 2½ to 3¼ inches; transverse in suture plane 2½ to 3¼ inches; and at right angles to suture plane 2¾ to 3¼ inches.
Suture: Inconspicuous to distinct line, extends from base toward apex but discontinues adjacent apex.
Ventral surface: Rounded, lightly lipped on most, lips generally unequal.
Cavity: Rounded, to slightly elongated in suture plane with suture showing on both sides; depth ½ to ⅝ inch; breadth ¾ to 1 inch; and markings the same yellow as on skin with red blush when exposed to sun.
Base: Retuse.
Apex: From emarginate to mucronate, pistil point slight and apical.
Stem: ¼ to ⅜ inch long, about ⅛ inch diameter, adherence to stone on some but not usual.
Skin: Medium thick, medium tender, tenacious to flesh; down, moderate to scant, short; color, mostly yellow 9–J–3 to 9–I–8 with red covering from none to half the surface, but averaging about one-fourth, and varying from 3–I–11 to 6–L–7 to 7–J–6.
Flesh: Color, clear bright yellow 9–K–6 with bright red 6–L–6 around the stone and in a few flecks in the adjacent flesh, and a very desirable color for freezing commercially; amygdalin, moderate; juice, moderate; texture, firm, fine, meaty, and buttery when frozen; fibers, few, fine, and tender; ripens, evenly; flavor, subacid, mild, and delicate; aroma, distinct; eating quality, good;
Stone: Color, from dark brown 48–L–9 to lighter brown 14–A–12 when first removed from the fruit; free; fibers, long; size, length 1⅛ to 1½ inches, breadth ⅞ to 1⅛ inches, thickness ⅜ to ⅞ inch; form, obovate, tip accuminate; base, straight to oblique; hilum, oval; apex, accuminate; sides, most nearly equal, some unequal; surface, generally with small pits and grooves near base, larger grooves and pits near apex; pits, irregularly shaped; ventral edge, thick with many fine grooves and some with larger grooves from base to apex; dorsal edge, narrow with generally one deep groove from base to apex; tendency to split, slight.
Use: General market, nearby and distant, and commercial freezing or canning.

Although the new variety of peach tree possesses the described characteristics under the ecological conditions prevailing at Exeter, Tulare County, Calif., having been first observed near Red Bluff, Tehama County, Calif., it is to be understood that variations of the usual magnitude in characteristics incident to the growing conditions, fertilization, pruning and pest control is to be expected.

Having thus described and illustrated my new variety of peach tree, what is claimed is:

1. A new and distinct peach tree substantially as illustrated and described and being characterized by its very late season of ripening, its good skin color for that season, a flesh texture and color found good for commercial freezing, and its ability to hold the fruit on the tree as ripening approaches, and mostly nearly resembling Merrill Halloween No. 1 (U.S. Plant Pat. 1,473), but an improvement on that variety by its higher skin color, its better freezing qualities, and its increased ability to hold fruit on the tree when approaching ripeness.

No references cited.

ROBERT E. BAGWILL, Primary Examiner